(12) United States Patent
Itamochi

(10) Patent No.: US 10,272,185 B2
(45) Date of Patent: Apr. 30, 2019

(54) CENTRIFUGAL PUMP

(71) Applicant: Terumo Kabushiki Kaisha, Tokyo (JP)

(72) Inventor: Yousuke Itamochi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 301 days.

(21) Appl. No.: 15/404,377

(22) Filed: Jan. 12, 2017

(65) Prior Publication Data

US 2017/0122337 A1 May 4, 2017

Related U.S. Application Data

(63) Continuation of application No. PCT/JP2015/073549, filed on Aug. 21, 2015.

(30) Foreign Application Priority Data

Sep. 19, 2014 (JP) .................................. 2014-191807

(51) Int. Cl.

| A61M 1/10 | (2006.01) |
|---|---|
| A61M 1/12 | (2006.01) |
| F04D 29/22 | (2006.01) |
| F04D 29/046 | (2006.01) |
| F04D 29/42 | (2006.01) |

(Continued)

(52) U.S. Cl.
CPC ............ *A61M 1/1013* (2014.02); *A61M 1/10* (2013.01); *A61M 1/101* (2013.01); *F04D 29/046* (2013.01); *F04D 29/0467* (2013.01); *F04D 29/22* (2013.01); *F04D 29/4273* (2013.01);

(Continued)

(58) Field of Classification Search
CPC ...... A61M 1/10; A61M 1/101; A61M 1/1013; A61M 1/122; F04D 29/046; F04D 29/22; F04D 29/4293
See application file for complete search history.

(56) References Cited

U.S. PATENT DOCUMENTS

| 5,360,317 A | 11/1994 | Clausen et al. |
|---|---|---|
| 5,527,159 A | 6/1996 | Bozeman, Jr. et al. |

(Continued)

FOREIGN PATENT DOCUMENTS

| JP | 4548450 B2 | 9/2010 |
|---|---|---|
| JP | 5739287 B2 | 6/2015 |

(Continued)

OTHER PUBLICATIONS

Supplementary European Search and Opinion Report, EP15842515, Mar. 6, 2018.

*Primary Examiner* — Leslie R Deak
(74) *Attorney, Agent, or Firm* — MacMillan, Sobanski & Todd, LLC

(57) ABSTRACT

A centrifugal pump for pumping blood in a circulatory support system has an inlet port configured to prevent or reduce formation of a thrombus in the blood. The centrifugal pump includes a housing with a main body, inlet and outlet ports, an impeller, and a support mechanism for the impeller. The support mechanism has a rod-like shaft member, and first and second bearings which rotatably support end portions of the shaft member. A lower surface of the first bearing is positioned at a distance from an inner peripheral surface of the blood inlet port from a central axis of the blood inlet port which is equal to or less than a distance from the central axis to the inner peripheral surface of the blood inlet port.

9 Claims, 6 Drawing Sheets

(51) Int. Cl.
   *F04D 7/04* (2006.01)
   *F04D 13/06* (2006.01)
(52) U.S. Cl.
   CPC ......... *F04D 29/4293* (2013.01); *A61M 1/122* (2014.02); *F04D 7/04* (2013.01); *F04D 13/06* (2013.01)

(56) References Cited

U.S. PATENT DOCUMENTS

| | | |
|---|---|---|
| 5,713,730 A | 2/1998 | Nosé et al. |
| 6,746,416 B2 | 6/2004 | Hubbard et al. |
| 2006/0084836 A1 | 4/2006 | Hubbard et al. |

FOREIGN PATENT DOCUMENTS

| | | |
|---|---|---|
| JP | 5743567 B2 | 7/2015 |
| WO | 9618358 A1 | 6/1996 | ional axis of the rotary shaft.

CENTRIFUGAL PUMP

CROSS REFERENCE TO RELATED APPLICATIONS

This application is a continuation of PCT Application No. PCT/JP2015/073549, filed Aug. 21, 2015, based on and claiming priority to Japanese application no. 2014-191807, filed Sep. 19, 2014, both of which are incorporated herein by reference in their entirety.

BACKGROUND OF THE INVENTION

The present invention relates to a bearing support for an impeller shaft in a centrifugal pump. In the related art, as blood pumps which transport blood, there have been known turbo-type pumps which send out blood in response to centrifugal force. The turbo-type pump includes a hollow housing, an impeller that is rotatably accommodated inside the housing, a rotary shaft (i.e., shaft member) that serves as a rotation center of the impeller, an upper bearing that rotatably supports an upper end portion of the rotary shaft, and a lower bearing that rotatably supports a lower end portion of the rotary shaft (see, e.g., Japanese patent 4548450).

In the blood pump disclosed in Japanese patent 4548450, the housing is provided with an inlet port through which blood flows in, and an outlet port through which blood flows out. The inlet port and the outlet port are tubularly formed so as to protrude from the housing. In addition, the inlet port is provided so as to be an extension of the shaft member such that a central axis thereof coincides with the rotational axis of the rotary shaft.

Recently, blood pumps in which the inlet port is provided so as to include an inclined section with respect to the rotary shaft have been adopted. The outer profile of the inclined inlet port intersects an intermediate portion of the shaft member, and the pump housing typically includes a recessed portion or pocket that is coaxially aligned with the shaft member and receives an upper bearing for the shaft member.

However, in such a configuration, due to the depth or the shape of the recessed portion as known in the art, when blood flows down through the inlet port then some blood tends to be retained inside the recessed portion. Therefore, in a case where the blood pump is used for a long time, there is a possibility that a thrombus may be formed inside the recessed portion of the rotary shaft, particularly in an outer peripheral portion of a bearing part which is inserted into the recessed portion of the rotary shaft.

SUMMARY OF INVENTION

Technical Problem

An object of the present invention is to provide a centrifugal pump in which a thrombus can be effectively prevented or restrained from being formed inside a blood inlet port.

Solution to Problem

Such an object is accomplished through following items (1) to (7) according to the present invention.

(1) A centrifugal pump includes a housing that is provided with a housing main body which is configured with a hollow body cavity. A blood inlet port is tubularly formed so as to protrude from the housing main body, which communicates with the housing main body, and through which blood flows in. A blood outlet port is provided at a different radial position from that of the blood inlet port in the housing main body and through which the blood flows out. A centrifugal force applying member (i.e., an impeller) is rotatably accommodated inside the hollow portion and rotates so as to apply centrifugal force to the blood. A support mechanism (e.g., shaft and bearings) supports the centrifugal force applying member such that the centrifugal force applying member can rotate with respect to the housing. The support mechanism is provided with a shaft member installed at a rotational center axis of the centrifugal force applying member, a first bearing which rotatably supports one end portion of the shaft member and is installed in an inner peripheral portion of the blood inlet port, and a second bearing which rotatably supports the other end portion of the shaft member. The blood inlet port has a proximal portion coaxial with the rotational center of the centrifugal force applying member and has a connection portion upstream of the proximal portion which inclines with respect to the rotation center of the centrifugal force applying member. The first bearing is provided with a blood flow path forming surface which faces an inner side of the blood inlet port and forms a flow path of the blood together with an inner peripheral surface of the blood inlet port. The blood flow path forming surface is positioned at a distance from a central axis of the blood inlet port that is equal to or less than a corresponding distance between the inner peripheral surface of the blood inlet port and the central axis of the blood inlet port.

(2) In the centrifugal pump according to (1), the blood inlet port is provided with a portion which inclines with respect to the rotation center of the centrifugal force applying member. The blood flow path forming surface is provided with a portion which inclines in the same direction as the inner peripheral surface of the blood inlet port.

(3) In the centrifugal pump according to (1) or (2), the blood inlet port has a cylindrical shape. The blood flow path forming surface is provided with a portion which is curved along a cylindrical shape of the inner peripheral surface of the blood inlet port.

(4) In the centrifugal pump according to any one of (1) to (3), the blood flow path forming surface has a multi-level structure deviated in a depth direction of the recessed portion and is provided with a first blood flow path forming surface and a second blood flow path forming surface which is positioned so as to be closer to the central axis of the blood inlet port than the first blood flow path forming surface.

(5) In the centrifugal pump according to (4), the first bearing has a columnar outer shape and is provided with a large-diameter portion and a small-diameter portion having outer diameters different from each other. The first blood flow path forming surface is a surface of the large-diameter portion facing the inner side of the blood inlet port. The second blood flow path forming surface is a surface of the small-diameter portion facing the inner side of the blood inlet port.

(6) In the centrifugal pump according to any one of (1) to (5), the first bearing is provided with a support surface which is in contact with one end surface of the shaft member so as to support the shaft member. The support surface is positioned so as to be closer to the central axis side of the blood inlet port than the inner peripheral surface of the blood inlet port.

(7) The centrifugal pump according to any one of (1) to (6) further includes a flow straightening portion that is formed so as to protrude toward an upstream side beyond the first bearing of the inner peripheral portion of the blood inlet port and straightens a flow of the blood.

ADVANTAGEOUS EFFECT OF INVENTION

According to the present invention, the blood flow path forming surface of the first bearing is positioned at the same distance as the inner peripheral surface of the blood inlet port from the central axis of the blood inlet port or is positioned so as to be closer to the central axis side of the blood inlet port than the inner peripheral surface of the blood inlet port. Therefore, the blood can smoothly flow down inside the blood inlet port, particularly on the periphery of the shaft member and the first bearing. Therefore, a thrombus can be effectively prevented or restrained from being formed inside the inlet port.

DETAILED DESCRIPTION OF PREFERRED EMBODIMENTS

Hereinafter, a centrifugal pump according to the present invention will be described in detail based on suitable embodiments illustrated in the accompanying drawings.

First Embodiment

Figure 1:
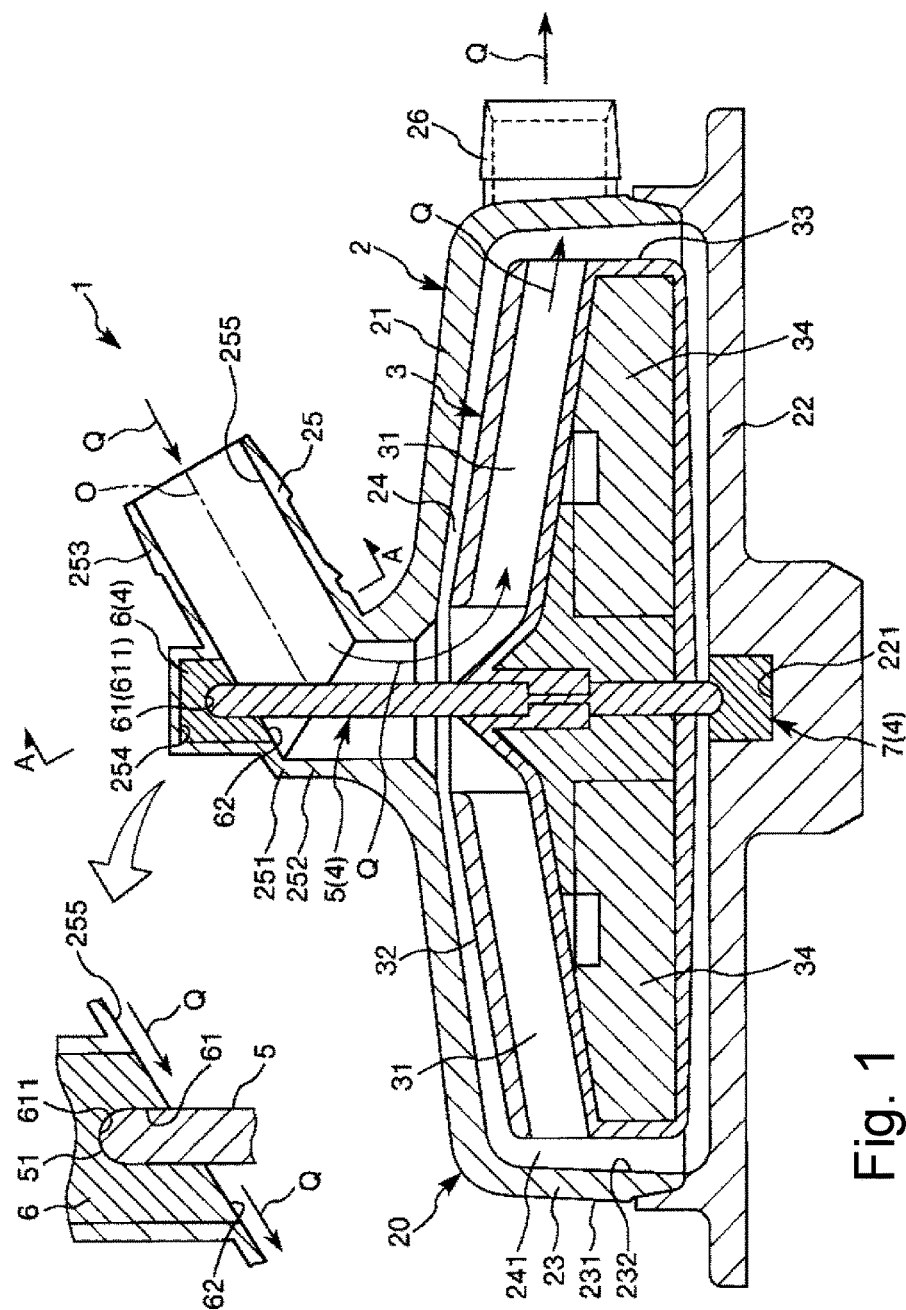
FIG. 1 is a cross-sectional side view illustrating an embodiment of a centrifugal pump, according to the present invention.
Figure 2:
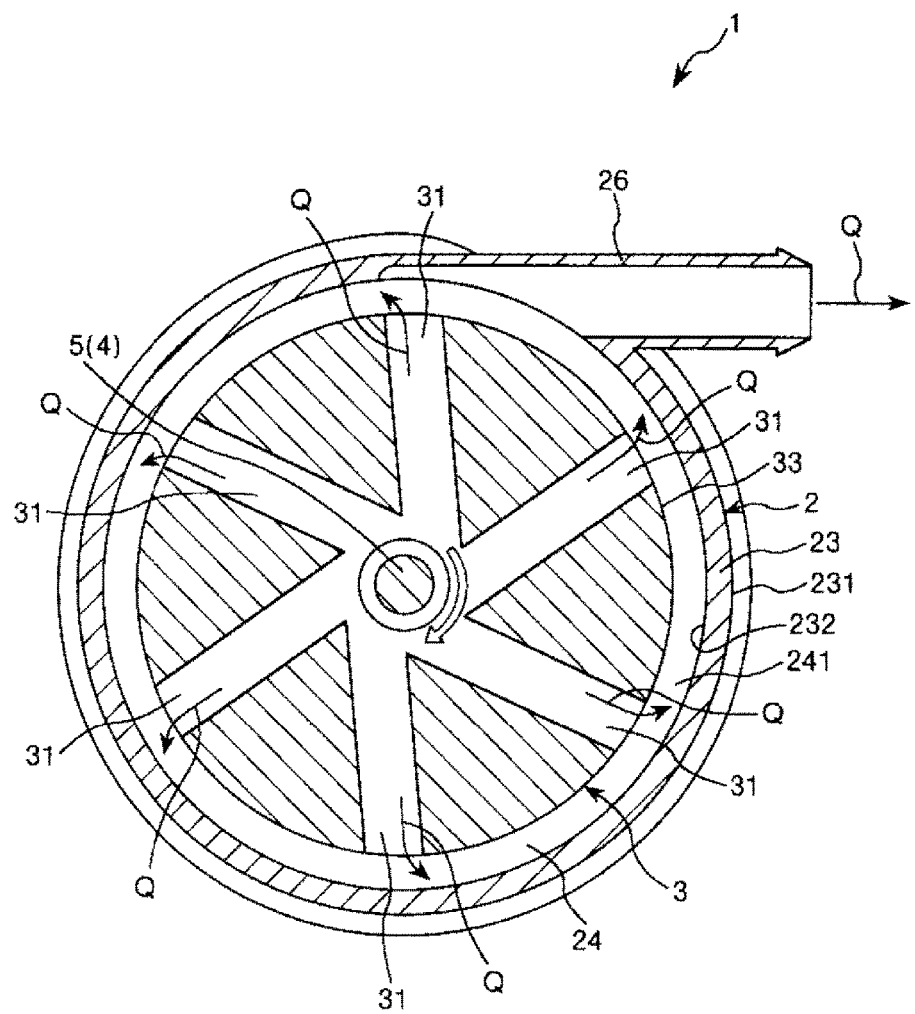
FIG. 2 is a cross-sectional plan view illustrating the embodiment of the centrifugal pump, according to the present invention.
Figure 3:
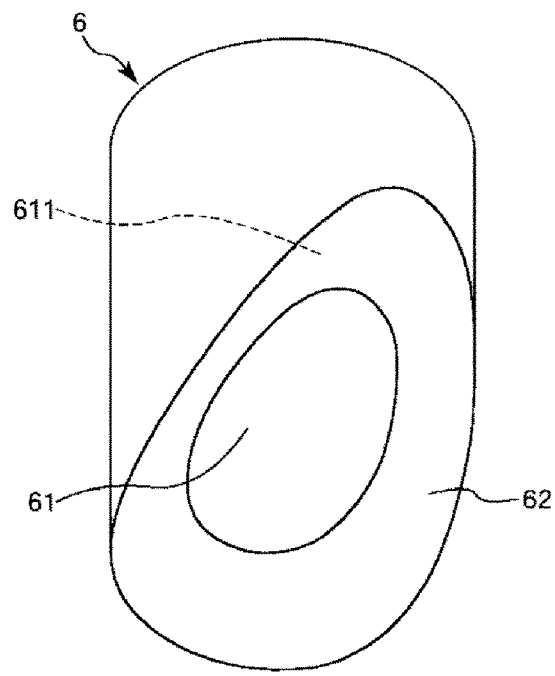
FIG. 3 is a perspective view of a first bearing provided in the centrifugal pump, according to the present invention.
Figure 4:
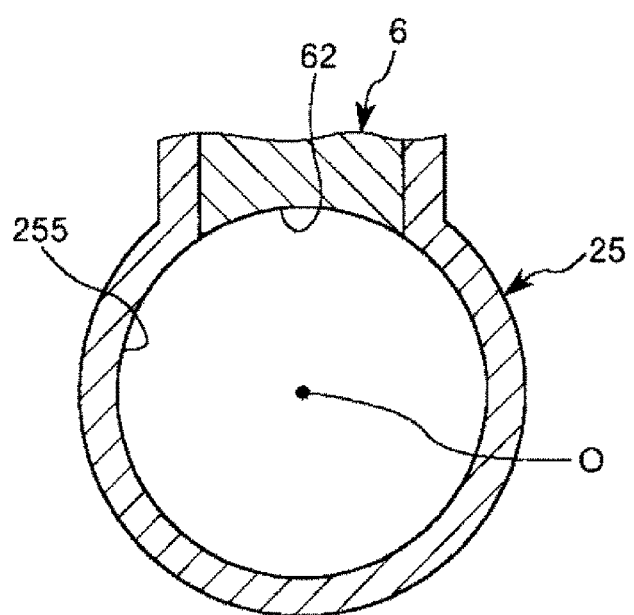
FIG. 4 is a cross-sectional view taken along line A-A in FIG. 1.

FIG. 1 is a cross-sectional side view illustrating a first embodiment of the centrifugal pump, according to the present invention. FIG. 2 is a cross-sectional plan view illustrating the first embodiment of the centrifugal pump, according to the present invention. FIG. 3 is a perspective view of a first bearing provided in the centrifugal pump, according to the first embodiment. FIG. 4 is a cross-sectional view taken along line A-A in FIG. 1. Note that, hereinafter, for convenience of description, in FIGS. 1 and 3 (in FIGS. 5 to 9 as well), the upper side will be referred to as "up" or "upward", and the lower side will be referred to as "down" or "downward".

A centrifugal pump 1 illustrated in FIG. 1 includes a housing 2 which is configured with a hollow body, a rotary body (impeller) 3 which is rotatably accommodated inside the housing 2, and a support mechanism 4 which supports the rotary body 3 such that the rotary body 3 can rotate with respect to the housing 2. Hereinafter, a configuration of each portion will be described.

The housing 2 is provided with a housing main body 20, a blood inlet port 25 through which blood Q flows in (such that blood Q is delivered to rotary body 3 in the area of its central rotational axis), and a blood outlet port 26 (receiving blood Q from an outer periphery of rotary body 3) through which the blood Q flows out.

The housing main body 20 is provided with a top plate 21 which is configured with a generally flat cylindrical cavity and blocks the upper end thereof, a side wall 23 which is erected from an edge portion of the top plate 21, and a bottom plate 22 which closes the lower end thereof. A flat space (hollow portion) surrounded by the top plate 21, the bottom plate 22, and the side wall 23 serves as a pump chamber 24.

The blood inlet port 25 and the blood outlet port 26 individually communicate with the pump chamber 24. The blood Q which has flowed in through the blood inlet port 25 can flow out through the blood outlet port 26 via the pump chamber 24.

As illustrated in FIG. 1, the blood inlet port 25 is tubularly (cylindrically) formed so as to protrude from a central portion of the top plate 21 (one end portion). An intermediate portion of the blood inlet port 25 in the longitudinal flow direction of port 25 is bent. A bent portion 251 serves as a boundary dividing the blood inlet port 25 into a proximal portion 252 on the top plate 21 side and a connection portion 253 on a side opposite thereto. Thus, proximal portion 252 and connection portion 253 generally define two intersecting cylinders with their central axes intersecting at bent portion 251. The connection portion 253 is provided so as to incline with respect to a rotary axis of the rotary body 3, and proximal portion 252 is coaxial with respect to the rotary axis of the rotary body 3. For example, a flexible tube for conveying blood through a blood circuit can be connected to the connection portion 253.

As illustrated in FIG. 2, the blood outlet port 26 is tubularly formed so as to protrude from the outer peripheral surface (outer peripheral portion) 231 of the side wall 23. The blood outlet port 26 protrudes toward a tangential direction of the outer peripheral surface 231 of the side wall 23.

Inside the pump chamber 24 of the housing main body 20, the rotary body 3 having a disk shape is concentrically disposed. The rotary body 3 is a centrifugal force applying member which rotates so as to apply centrifugal force to the blood Q.

As illustrated in FIG. 2, the rotary body 3 is provided with a plurality of blood flow paths 31 (six in the illustrated configuration) through which the blood Q passes. The blood flow paths 31 are formed radially from the center of the rotary body 3. In addition, portions of the blood flow paths 31 at the axial center of the rotary body 3 meet (intersect) each other and are open on an upper surface 32 of the rotary body 3. Meanwhile, the opposite ends of the blood flow paths 31 are open to an outer peripheral surface 33 of the rotary body 3. In addition, a gap 241 is formed between the outer peripheral surface 33 of the rotary body 3 and an inner peripheral surface 232 of the side wall 23 of the housing 2.

When the above-described rotary body 3 rotates clockwise around a shaft member 5 as illustrated in FIG. 2 in which the housing 2 is viewed from above, the blood Q flowing in through the blood inlet port 25 enters each of the blood flow paths 31 from the portion on the center side of the rotary body 3, and the blood Q flows down through the blood flow paths 31 upon reception of centrifugal force. The flowed-down blood Q flows out to the gap 241. Thereafter, the blood Q receives clockwise rotary force in the gap 241 as illustrated in FIG. 2. When the blood Q arrives at the blood outlet port 26, the blood Q is reliably discharged through the blood outlet port 26.

As illustrated in FIG. 1, in the rotary body 3, magnets are respectively installed at portions on the lower side of the blood flow paths 31. Note that, in the configuration illustrated in FIG. 1, a plurality of (for example, six) permanent magnets 34 are adopted. When the centrifugal pump 1 is driven, the centrifugal pump 1 is mounted with external drive means (not illustrated) with the bottom plate 22 of the housing 2 down so that the below-described shaft member 5 is parallel to the vertical direction. In this mounted state, the centrifugal pump 1 is used. For example, the external drive means is provided with a motor and a permanent magnet which is interlocked with the motor. The permanent magnet and the permanent magnets 34 built in the centrifugal pump 1 attract each other due to magnetic force. When the motor rotates in such a state, rotary force thereof is transferred via the magnets attracting each other, and thus, the rotary body 3 can also rotate.

Note that, the diameter of the rotary body 3 is not particularly limited. For example, the diameter preferably ranges from 20 to 200 mm and more preferably ranges from 30 to 100 mm. The thickness (i.e., vertical height) of the rotary body 3 is not particularly limited. For example, the thickness preferably ranges from 3 to 40 mm and more preferably ranges from 5 to 30 mm. The maximum speed of the rotary body 3 is not particularly limited. For example, the maximum speed preferably ranges from 2,000 to 6,000 rpm and more preferably ranges from 2,500 to 5,000 rpm.

In addition, the configuration material of the rotary body 3 and the housing 2 is not particularly limited. Examples of the materials include an acryl-based resin such as rigid polyvinyl chloride, polyethylene, polypropylene, polystyrene, polycarbonate, an acrylic resin, and polymethyl methacrylate (PMMA); polyester such as polyethylene terephthalate (PET) and polybutylene terephthalate (PBT); polysulfone; and various types of rigid resins such as polyarylate. In addition, among the above-referenced configuration materials, polycarbonate and an acrylic resin are particularly preferable in compatibility with the blood Q, excellent transparency, and molding processability.

As illustrated in FIG. 1, the rotary body 3 is supported via the support mechanism 4 so as to be rotatable with respect to the housing 2. The support mechanism 4 is provided with the shaft member 5, a first bearing 6 which rotatably supports the upper end portion (one end portion) of the shaft member 5, and a second bearing 7 which rotatably supports the lower end portion (the other end portion) of the shaft member 5.

The shaft member 5 is installed at the rotational center axis of the rotary body 3. The shaft member 5 is a rod-like member having both end portions rounded. In a case where ceramic is adopted as the configuration material of the shaft member 5, when the end portions of the shaft member 5 are subjected to grinding, sliding characteristics of both the end portions during rotation of the shaft member 5 are improved. In a case where a metallic material is adopted as the configuration material of the shaft member 5, both the end portions of the shaft member 5 may be subjected to coating with diamond-like carbon (DLC) or titanium, for example, to resist grinding. Accordingly, sliding characteristics and durability of both the end portions during rotation of the shaft member 5 are improved.

The first bearing 6 is fixedly installed in a first bearing installation portion (recessed portion) 254 which is formed so as to be recessed in an inner peripheral portion of the connection portion 253 of the blood inlet port 25 (i.e., upstream of bent portion 251). The second bearing 7 is fixedly installed in a second bearing installation portion 221 which is formed so as to be recessed in the central portion of the bottom plate 22 of the housing 2. Note that, the method of fixing the first bearing 6 and the second bearing 7 with respect to the housing 2 is not particularly limited. Examples of the method include a method performed through press fitting, a method performed through adhering (adhering performed with an adhesive or a solvent), a method performed through welding (heat-welding, high-frequency welding, ultrasound welding, and the like), and a method performed through insert molding.

As illustrated in FIGS. 1 and 3, the first bearing 6 has a columnar outer shape and extends coaxially with respect to the rotational center axis direction of the rotary body 3. The first bearing 6 is provided with an insertion portion (bore) 61 into which the upper end portion of the shaft member 5 is inserted. The insertion portion 61 is a recessed portion open at a lower surface 62 of the first bearing 6. In addition, the bottom portion (i.e., internal terminus) of the insertion portion 61 serves as a support surface 611 which is in contact with the upper end surface of the shaft member 5 so as to support the upper end surface thereof and is curved in order to smoothly receive the shaped upper end surface of the shaft member 5.

The lower surface 62 (which is blood flow path forming surface) of the first bearing 6 faces the inner flow region of the blood inlet port 25 and forms a flow path surface together with an inner peripheral surface 255 of the blood inlet port 25 (connection portion 253). The lower surface 62 of the first bearing 6 inclines in the same direction and at the same inclination angle as the inner peripheral surface 255 of the blood inlet port 25. In addition, the lower surface 62 of the first bearing 6 is positioned at the same radial distance as the inner peripheral surface 255 of the blood inlet port 25 from a central axis O of the blood inlet port 25 (connection portion 253). In other words, the lower surface 62 of the first bearing 6 and the inner peripheral surface 255 of the blood inlet port 25 form a continuous surface having no step at the boundary portion therebetween, and it can be said that the lower surface 62 of the first bearing 6 in the blood inlet port 25 is located at the same position in the radial direction as the inner peripheral surface 255 of the blood inlet port 25.

According to such a configuration, it is possible to eliminate any steps that could otherwise retain the blood Q. Accordingly, as illustrated in the enlarged portion in FIG. 1, when the blood Q flowing down inside the blood inlet port 25 flows down in the vicinity of the boundary portion between the inner peripheral surface 255 of the blood inlet port 25 and the lower surface 62 of the first bearing 6, the blood Q can smoothly flow down. Therefore, a retention portion (e.g., a dead zone) which can retain the blood Q can be effectively prevented or restrained from being generated inside the blood inlet port 25. As a result thereof, a thrombus can be effectively prevented or restrained from being formed inside the blood inlet port 25 (particularly, in the outer peripheral portion of the shaft member 5). Moreover, since the step which can retain the blood Q is eliminated, air bubbles can be easily removed while the centrifugal pump 1 is filled with blood at the time of beginning of use. In a case where air bubbles are intermixed with the blood Q, the air bubbles can also be prevented from being retained.

In addition, as illustrated in FIG. 4, the lower surface 62 of the first bearing 6 is curved at the same curvature as the circumferential curvature of the inner peripheral surface 255 of the blood inlet port 25. Therefore, in the cross section illustrated in FIG. 4, the lower surface 62 of the first bearing 6 forms a circular inner surface together with the inner peripheral surface 255 of the blood inlet port 25. Accordingly, the blood Q can more smoothly flow down inside the blood inlet port 25.

It is preferable that the first bearing 6 and the second bearing 7 are formed of the same materials. In addition, the bearings and the shaft member 5 may be formed of the same materials as each other or may be formed of materials different from each other. In a case where the bearings and the shaft member 5 are formed of the same materials as each other, a rigid material is adopted as each of the configuration materials. For example, each of the first bearing 6, the second bearing 7, and the shaft member 5 can be formed of a metallic material or ceramic. In a case where the bearings and the shaft member 5 are formed of materials different from each other, a rigid material is adopted as the configuration material of the shaft member 5, and a material softer than the shaft member 5 is adopted as the configuration material of the bearings. For example, the shaft member 5 can be formed of a metallic material or ceramic, and each of the first bearing 6 and the second bearing 7 can be formed of a resin material.

The resin material is not particularly limited. Examples of the resin materials include polyethylene; polypropylene; polyolefin such as an ethylene-vinyl acetate copolymer; modified polyolefin; polyamide (for example: nylon 6, nylon 46, nylon 66, nylon 610, nylon 612, nylon 11, nylon 12, nylon 6-12, and nylon 6-66); thermoplastic polyimide; a liquid crystal polymer such as aromatic polyester; polyphenylene oxide; polyphenylene sulfide; polycarbonate; polymethyl methacrylate; polyether; polyether ether ketone; polyether imide; polyacetal; various types of thermoplastic elastomers such as a styrene-based elastomer, a polyolefin-based elastomer, a polyvinyl chloride-based elastomer, a polyurethane-based elastomer, a polyester-based elastomer, a polyamide-based elastomer, a polybutadiene-based elastomer, a trans-polyisoprene-based elastomer, a fluorine rubber-based elastomer, and a chlorinated polyethylene-based elastomer; and copolymers, blends, polymer alloys, and the like having these as a main ingredient. Among these, it is possible to adopt one type, or two or more types in a mixed state. Among these, it is particularly preferable to adopt polyethylene (super-high-molecular polyethylene) having a significant average molecular weight (for example, approximately two millions to ten millions). Particularly, when the first bearing 6 is formed of super-high-molecular polyethylene, abrasion resistance, processability, and self-lubricating characteristics of the first bearing 6 can be improved.

The metallic material is not particularly limited. Examples of the metallic material include stainless steel or the like. In addition to the metallic material, ceramic and the like can also be adopted. In addition, hardness (Vickers hardness (Hv)) of such a rigid material (the metallic material, or ceramic) is not particularly limited. For example, the hardness is preferably 50 or greater and is more preferably 100 or greater.

Second Embodiment

Figure 5:
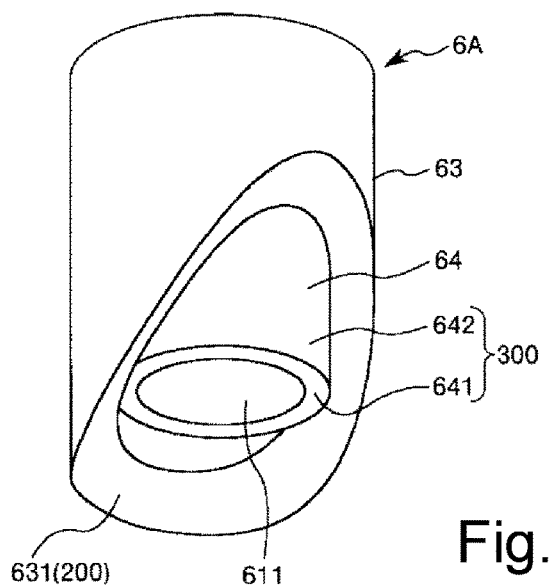
FIG. 5 is a perspective view of a second embodiment of a first bearing provided in a centrifugal pump, according to the present invention.
Figure 6:
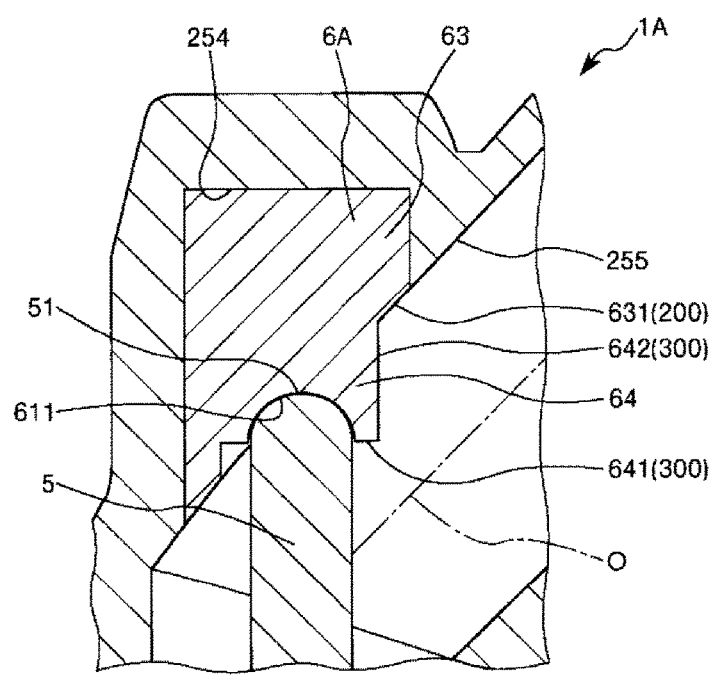
FIG. 6 is an enlarged cross-sectional view of a second embodiment of the centrifugal pump according to the present invention.

FIG. 5 is a perspective view of a first bearing provided in a centrifugal pump (second embodiment), according to the present invention. FIG. 6 is an enlarged cross-sectional view of the centrifugal pump (second embodiment) according to the present invention.

Hereinafter, with reference to the views, the second embodiment of the centrifugal pump according to the present invention will be described. The points different from those of the aforementioned embodiment will be mainly described, and description of similar elements will be omitted.

The present embodiment is similar to the first embodiment except that the shape of the first bearing is different therefrom.

As illustrated in FIGS. 5 and 6, a first bearing 6A of a centrifugal pump 1A is provided with a large-diameter portion 63 and a small-diameter portion 64 having outer diameters different from each other.

The large-diameter portion 63 is a portion adapted to be inserted into the first bearing installation recess 254. A surface of the large-diameter portion 63 facing the inside of the blood inlet port 25, that is, a lower surface 631 (hereinafter, will also be referred to as "first blood flow path forming surface 200") inclines in the same direction and at the same inclination angle as the inner peripheral surface 255 of the blood inlet port 25. In addition, the lower surface 631 of the large-diameter portion 63 is positioned at the same distance as the inner peripheral surface 255 of the blood inlet port 25 from the central axis O of the blood inlet port 25 (connection portion 253) in the radial direction. Moreover, the lower surface 631 of the large-diameter portion 63 is curved at the same curvature as the circumferential curvature of the inner peripheral surface 255 of the blood inlet port 25. According to the above-described large-diameter portion 63, a smooth flow of the blood Q can be ensured.

The small-diameter portion 64 is positioned so as to extend closer to the central axis O side of the blood inlet port 25 than the large-diameter portion 63. A lower surface 641 of the small-diameter portion 64 is a surface perpendicular to the rotation center of the shaft member 5. Note that, a second blood flow path forming surface 300 is configured with the lower surface 641 of the small-diameter portion 64 and an outer peripheral surface 642.

In addition, in the small-diameter portion 64, the insertion portion 61 of the first embodiment is omitted, and the curved support surface 611 depressed along the upper end surface of the shaft member 5 is formed without an initial cylindrical passage. Accordingly, the length of a portion of the shaft member 5 inserted into the first bearing 6 can be minimized as much as possible.

In addition, as illustrated in FIG. 6, the support surface 611 is positioned so as to be closer to the central axis O side of the blood inlet port 25 than the inner peripheral surface 255 of the blood inlet port 25, thereby exposing the interface between shaft member 5 and first bearing 6A to a direct blood flow within inlet port 25. Accordingly, the blood Q which has entered a gap between an upper end surface 51 of the shaft member 5 and the support surface 611 is pushed out by the blood Q flowing down through the blood inlet port 25. Therefore, the blood Q can be effectively prevented or restrained from being retained in the gap between the upper end surface 51 of the shaft member 5 and the support surface 611. As a result thereof, the blood Q can prevent or restrain a thrombus from being formed between the upper end surface 51 of the shaft member 5 and the support surface 611.

In this manner, in the first bearing 6A, the surface facing the inside of the blood inlet port 25 has a multi-level structure in which the first blood flow path forming surface 200 and the second blood flow path forming surface 300 are deviated from each other along the longitudinal direction of the first bearing 6A. According to such a configuration, a smooth blood flow can be ensured by the large-diameter portion 63, and the small-diameter portion 64 can prevent or restrain a thrombus from being formed between the upper end surface 51 of the shaft member 5 and the support surface 611.

Third Embodiment

Figure 7:
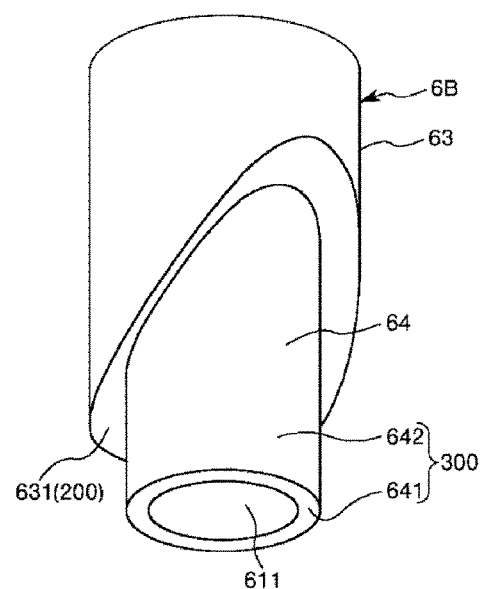
FIG. 7 is a perspective view of a third embodiment of a first bearing provided in a centrifugal pump, according to the present invention.
Figure 8:
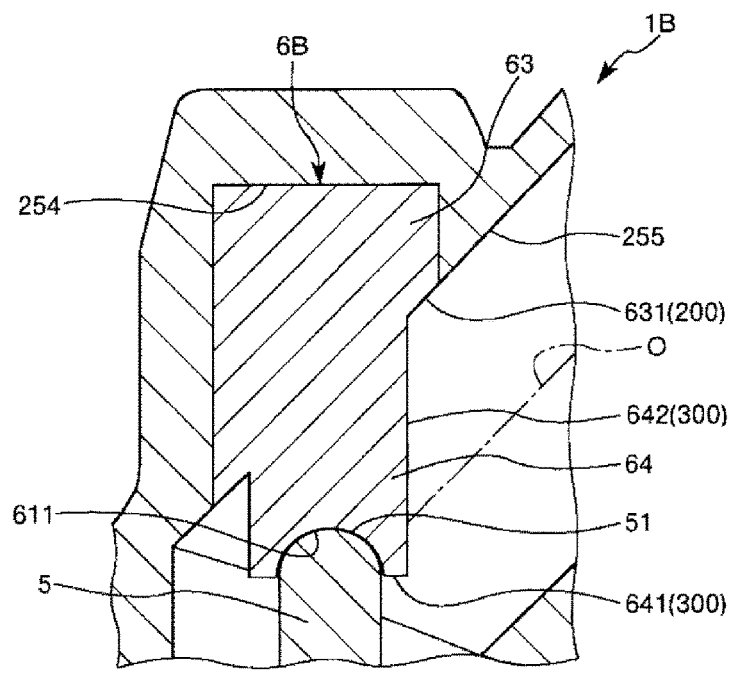
FIG. 8 is an enlarged cross-sectional view of a third embodiment of a centrifugal pump according to the present invention.

FIG. 7 is a perspective view of a first bearing provided in a centrifugal pump (third embodiment), according to the present invention. FIG. 8 is an enlarged cross-sectional view of the centrifugal pump (third embodiment) according to the present invention.

Hereinafter, with reference to the views, the third embodiment of the centrifugal pump according to the present invention will be described. The points different from those of the aforementioned embodiments will be mainly described, and description of similar elements will be omitted. The present embodiment is similar to the second embodiment except that the shape (e.g., length) of a small-diameter portion is different therefrom.

As illustrated in FIGS. 7 and 8, in a first bearing 6B of a centrifugal pump 1B, the small-diameter portion 64 is longer than the small-diameter portion of the second embodiment. In addition, the second blood flow path forming surface 300 (particularly, the lower surface 641) is positioned so as to be closer to the central axis O than the lower surface 631 of the large-diameter portion 63 in the radial direction of the blood inlet port 25. In the present embodiment, the lower surface 641 of the small-diameter portion 64 preferably intersects the central axis O. Therefore, the support surface 611 is positioned in the vicinity of the central axis O. Therefore, in the vicinity of the central axis O of the blood inlet port 25, the support surface 611 is positioned in a portion where the flow rate of the blood Q is relatively fast. Accordingly, the blood Q which has entered the gap between the upper end surface 51 of the shaft member 5 and the support surface 611 is more reliably pushed out by the blood Q flowing down through the blood inlet port 25. Therefore, the blood Q can be more reliably prevented or restrained from being retained in the gap between the upper end surface 51 of the shaft member 5 and the support surface 611. As a result thereof, a thrombus can be more effectively prevented or restrained from being formed between the upper end surface 51 of the shaft member 5 and the support surface 611.

Fourth Embodiment

Figure 9:
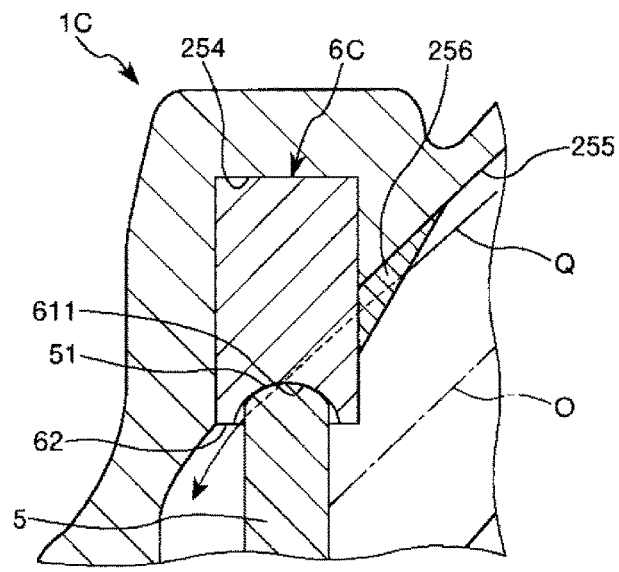
FIG. 9 is an enlarged cross-sectional view of a fourth embodiment of a centrifugal pump according to the present invention.
Figure 10:
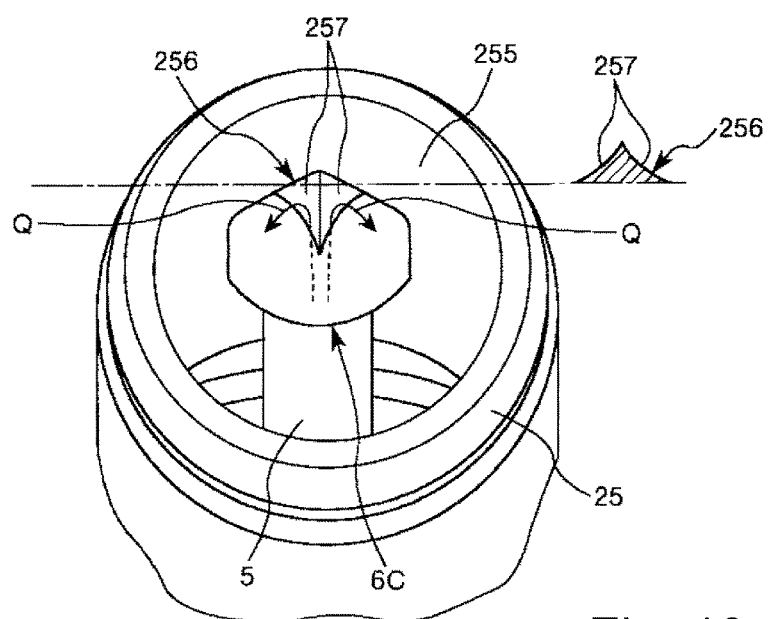
FIG. 10 is a view wherein the centrifugal pump of the fourth embodiment is viewed from an opening side of a blood inlet port.

FIG. 9 is an enlarged cross-sectional view of a centrifugal pump (fourth embodiment), according to the present invention. FIG. 10 is a view when the centrifugal pump (fourth embodiment) according to the present invention is viewed from an open end of a blood inlet port.

Hereinafter, with reference to the views, the fourth embodiment of the centrifugal pump according to the present invention will be described. The points different from those of the aforementioned embodiments will be mainly described, and description of similar elements will be omitted.

The present embodiment is substantially similar to the aforementioned first embodiment except that a flow straightening portion is provided and the shape of the first bearing is different therefrom.

As illustrated in FIGS. 9 and 10, in a first bearing 6C of a centrifugal pump 1C, the lower surface 62 is perpendicular to the depth direction of the first bearing installation portion 254. In addition, the lower surface 62 is positioned so as to be closer to the central axis O side in the radial direction of the blood inlet port 25 than the inner peripheral surface 255 of the blood inlet port 25 (i.e., lower surface 62 is within the cylindrical projection of peripheral surface 255).

In addition, a flow straightening portion 256 which is provided on the upstream side of the first bearing 6 and which rectifies the flow of the blood Q is integrally formed in the blood inlet port 25. The flow straightening portion 256 is provided so as to protrude toward the central axis O side from the inner peripheral surface 255 of the blood inlet port 25. In addition, the flow straightening portion 256 extends in the direction central axis O. Due to the flow straightening portion 256, the blood Q flowing down through the blood inlet port 25 is deflected such that it flows on both sides via the flow straightening portion 256 (refer to FIG. 10). Accordingly, the blood Q flows down inside the blood inlet port 25 so as to bypass the first bearing 6 which is positioned on the downstream side of the flow straightening portion 256. Therefore, the blood Q can be more effectively prevented or restrained from being retained on the periphery of the first bearing 6. Therefore, a thrombus can be more effectively prevented or restrained from being formed in the outer peripheral portion of the first bearing 6.

In addition, the cross-sectional shape of the flow straightening portion 256 forms a substantial triangle having the apex on the central axis O side. As illustrated in FIG. 10, in the flow straightening portion 256, the width and the protruding height gradually become smaller toward the upstream side. Accordingly, the blood Q flowing down through the blood inlet port 25 is gently straightened from the upstream side.

Moreover, as illustrated in the auxiliary cross-sectional view of FIG. 10, a pair of side surfaces 257 of the flow straightening portion 256 is curved in a direction of approaching each other. Accordingly, the blood Q flowing down through the blood inlet port 25 is more gently straightened from the upstream side.

According to such a configuration, the flow straightening portion 256 can more reliably exhibit the above-described effect.

In addition, the end portion of the flow straightening portion 256 on the downstream side is in contact with the outer peripheral portion of the first bearing 6C. Accordingly, for example, force which can be generated in the radial direction when the rotary body 3 rotates is applied to the first bearing 6C. Therefore, the flow straightening portion 256 can act as a stiffening rib to prevent the first bearing 6C from being deformed, that is, the flow straightening portion 256 can function as a reinforcement portion. As a result thereof, it is possible to achieve a long service life of the centrifugal pump 1C. Moreover, it is possible to reduce the influence to the first bearing 6C caused due to the fluid pressure of the blood Q, and thus, damage to blood can be reduced.

Hereinbefore, the centrifugal pump according to the present invention has been described with reference to the illustrated embodiments. The present invention is not limited thereto. Each of the portions configuring the centrifugal pump can be replaced with an arbitrarily configured portion which can exhibit the same function. In addition, an arbitrarily configured element may be added thereto.

Note that, in the first embodiment, the lower surface of the first bearing is positioned at the same distance as the inner peripheral surface of the blood inlet port from the central axis of the blood inlet port. However, the present invention is not limited thereto. The lower surface thereof may be positioned so as to be closer to the central axis side of the blood inlet port than the inner peripheral surface of the blood inlet port.

In addition, in each of the embodiments, the bearings and the housing are configured to be separate from each other. However, the present invention is not limited thereto. The bearings and the housing may be integrally configured.

In addition, in the second embodiment, the lower surface of the large-diameter portion in the blood inlet port is located at the same position in the radial direction as the inner peripheral surface of the blood inlet port. However, the present invention is not limited thereto. The lower surface thereof may be positioned so as to be closer to the central axis side of the blood inlet port than the inner peripheral surface of the blood inlet port.

In addition, in the second embodiment and the third embodiment, the lower surface of the small-diameter portion is perpendicular to the longitudinal direction of the first bearing. However, the present invention is not limited thereto. The lower surface thereof may incline.

In addition, in the fourth embodiment, the flow straightening portion extends in the central axis direction of the blood inlet port. However, the present invention is not limited thereto. For example, flow straightening portions may be intermittently provided by causing the blood inlet port to be sparsely absent in the longitudinal direction.

In addition, in the fourth embodiment, the cross-sectional shape of the flow straightening portion substantially forms a triangle. However, the present invention is not limited thereto. For example, the cross-sectional shape thereof may be circular, a semicircle, a square, or a polygon having more sides.

In addition, in the fourth embodiment, the downstream side of the flow straightening portion is in contact with the first bearing. However, the present invention is not limited thereto. The downstream side thereof may be separated from the first bearing.

In addition, in the fourth embodiment, the flow straightening portion is integrally formed with the housing (blood inlet port). However, the present invention is not limited thereto. The rectification portion may be configured to be separate from the housing or may be integrally formed with the first bearing.

What is claimed is:

1. A centrifugal pump comprising:
a housing having a housing main body enclosing a hollow body cavity, wherein the main body defines a blood inlet port which is tubularly formed so as to protrude from the housing main body and which communicates with the hollow body cavity, and wherein the main body defines a blood outlet port which is provided at a position different from that of the blood inlet port in the housing main body and through which the blood flows out;
a centrifugal force applying member that is rotatably accommodated inside the hollow body cavity and rotates to apply centrifugal force to the blood; and
a support mechanism that supports the centrifugal force applying member such that the centrifugal force applying member can rotate with respect to the housing;
wherein the support mechanism comprises a shaft member which is installed along a rotational center of the centrifugal force applying member, a first bearing which rotatably supports one end portion of the shaft member and extends through an inner peripheral portion of the blood inlet port, and a second bearing which rotatably supports the other end portion of the shaft member;
wherein the blood inlet port has a proximal portion coaxial with the rotational center of the centrifugal force applying member and has a connection portion upstream of the proximal portion which inclines with respect to the rotation center of the centrifugal force applying member;
wherein the first bearing is provided with a blood flow path forming surface which faces an inner side of the blood inlet port and forms a flow path of the blood together with an inner peripheral surface of the blood inlet port; and
wherein the blood flow path forming surface is positioned at a distance from a central axis of the blood inlet port that is equal to or less than a corresponding distance between the inner peripheral surface of the blood inlet port and the central axis of the blood inlet port.

2. The centrifugal pump according to claim 1 wherein the blood flow path forming surface is provided with a portion which inclines in the same direction as the inner peripheral surface of the blood inlet port.

3. The centrifugal pump according to claim 1:
wherein the blood inlet port has a cylindrical shape, and
wherein the blood flow path forming surface is provided with a portion which is curved along a curved shape of the inner peripheral surface of the blood inlet port.

4. The centrifugal pump according to claim 1:
wherein the blood flow path forming surface has a multi-level structure deviated in a depth direction of the recessed portion and is provided with a first blood flow path forming surface and a second blood flow path forming surface which is positioned so as to be closer to the central axis side of the blood inlet port than the first blood flow path forming surface.

5. The centrifugal pump according to claim 4:
wherein the first bearing has a columnar outer shape and is provided with a large-diameter portion and a small-diameter portion having outer diameters different from each other;
wherein the first blood flow path forming surface is a surface of the large-diameter portion facing the inner side of the blood inlet port; and
wherein the second blood flow path forming surface is a surface of the small-diameter portion facing the inner side of the blood inlet port.

6. The centrifugal pump according to claim 1:
wherein the first bearing is provided with a support surface which is in contact with one end surface of the shaft member so as to support the shaft member, and
wherein the support surface is positioned so as to be closer to the central axis side of the blood inlet port than the inner peripheral surface of the blood inlet port.

7. The centrifugal pump according to claim 1 further comprising:
a flow straightening portion that is formed so as to protrude toward an upstream side beyond the first bearing of the inner peripheral portion of the blood inlet port and straightens a flow of the blood.

8. The centrifugal pump according to claim 7 wherein the flow straightening portion has a substantially triangular cross section with an apex directed toward the central axis of the blood inlet port.

9. The centrifugal pump according to claim 7 wherein the flow straightening portion is in contact with the first bearing to reinforce the blood inlet port.

\* \* \* \* \*